(12) United States Patent
Baynham

(10) Patent No.: US 9,421,111 B2
(45) Date of Patent: Aug. 23, 2016

(54) PLIF HINGED SPACER

(71) Applicant: Atlas Spine, Inc., Jupiter, FL (US)

(72) Inventor: Matthew G. Baynham, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 0 days.

(21) Appl. No.: 14/214,511

(22) Filed: Mar. 14, 2014

(65) Prior Publication Data

US 2014/0277508 A1   Sep. 18, 2014

Related U.S. Application Data

(60) Provisional application No. 61/800,739, filed on Mar. 15, 2013.

(51) Int. Cl.
*A61F 2/44* (2006.01)
*A61F 2/30* (2006.01)

(52) U.S. Cl.
CPC .............. *A61F 2/447* (2013.01); *A61F 2/442* (2013.01); *A61F 2/4455* (2013.01); *A61F 2002/30156* (2013.01); *A61F 2002/30373* (2013.01); *A61F 2002/30471* (2013.01); *A61F 2002/30543* (2013.01); *A61F 2002/30579* (2013.01); *A61F 2002/30604* (2013.01); *A61F 2002/30904* (2013.01); *A61F 2002/4475* (2013.01); *A61F 2310/00017* (2013.01); *A61F 2310/00023* (2013.01)

(58) Field of Classification Search
CPC . A61F 2/44; A61F 2/4455; A61F 2002/4475; A61F 2002/3093
USPC ................. 606/246–249; 623/17.11–17.16
See application file for complete search history.

(56) References Cited

U.S. PATENT DOCUMENTS

| 5,653,763 | A | * | 8/1997 | Errico et al. | 623/17.11 |
| 6,015,436 | A | | 1/2000 | Schonhoffer | |
| 6,090,143 | A | * | 7/2000 | Meriwether et al. | 623/17.11 |
| 6,120,506 | A | | 9/2000 | Kohrs et al. | |
| 6,562,074 | B2 | | 5/2003 | Gerbec et al. | |
| 6,648,917 | B2 | * | 11/2003 | Gerbec et al. | 623/17.11 |
| 6,821,298 | B1 | * | 11/2004 | Jackson | 623/17.15 |
| 7,211,112 | B2 | | 5/2007 | Baynham et al. | |
| 7,850,733 | B2 | | 12/2010 | Baynham et al. | |
| 8,273,129 | B2 | | 9/2012 | Baynham et al. | |
| 2005/0177235 | A1 | * | 8/2005 | Baynham et al. | 623/17.11 |

* cited by examiner

*Primary Examiner* — Mary Hoffman
*Assistant Examiner* — Tara R Carter
(74) *Attorney, Agent, or Firm* — McHale & Slavin, P.A.

(57) ABSTRACT

A spinal implant formed from a hinged distractor having an upper and lower support body that is hinged by use of pinions. An insert body is constructed and arranged to slide between the section to expand and maintain a space therebetween. The insert body includes a leading edge that is tapered to allow ease of insertion. A trailing edge that extends beyond a front edge of the upper support body will cause the insert body to be locked into position. A trailing edge engages the rear of the upper support body to prevent over insertion. A lower surface of the insert body may include locking surfaces.

10 Claims, 6 Drawing Sheets

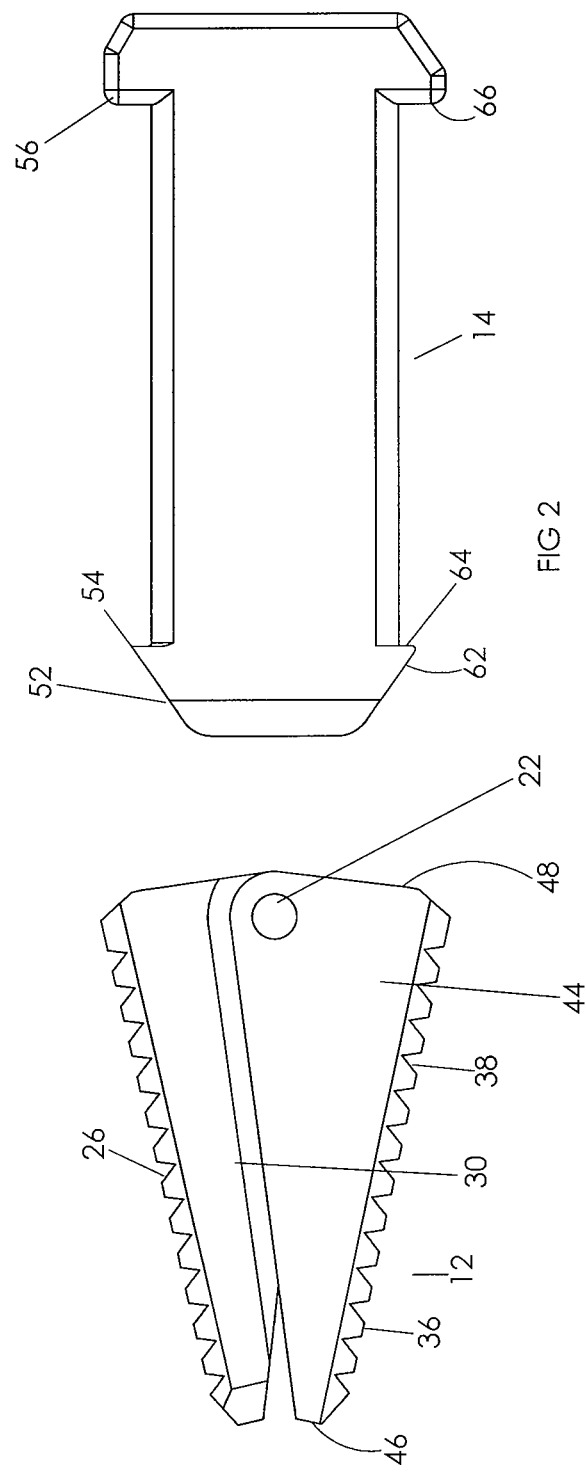

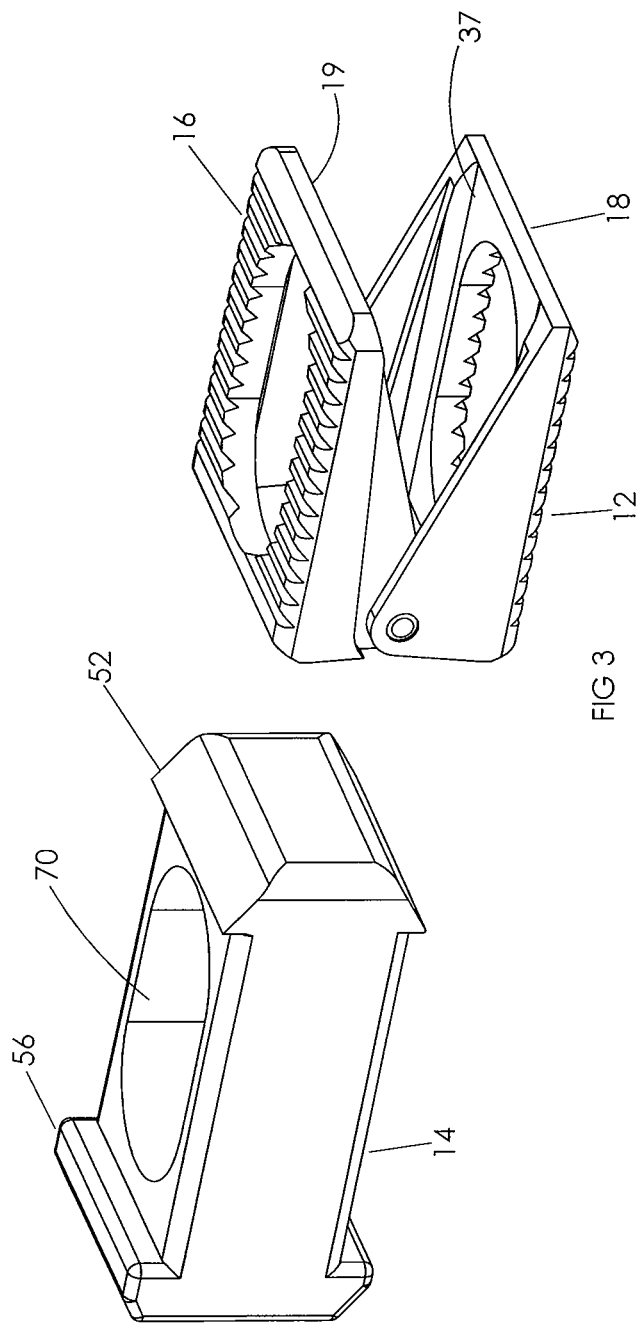

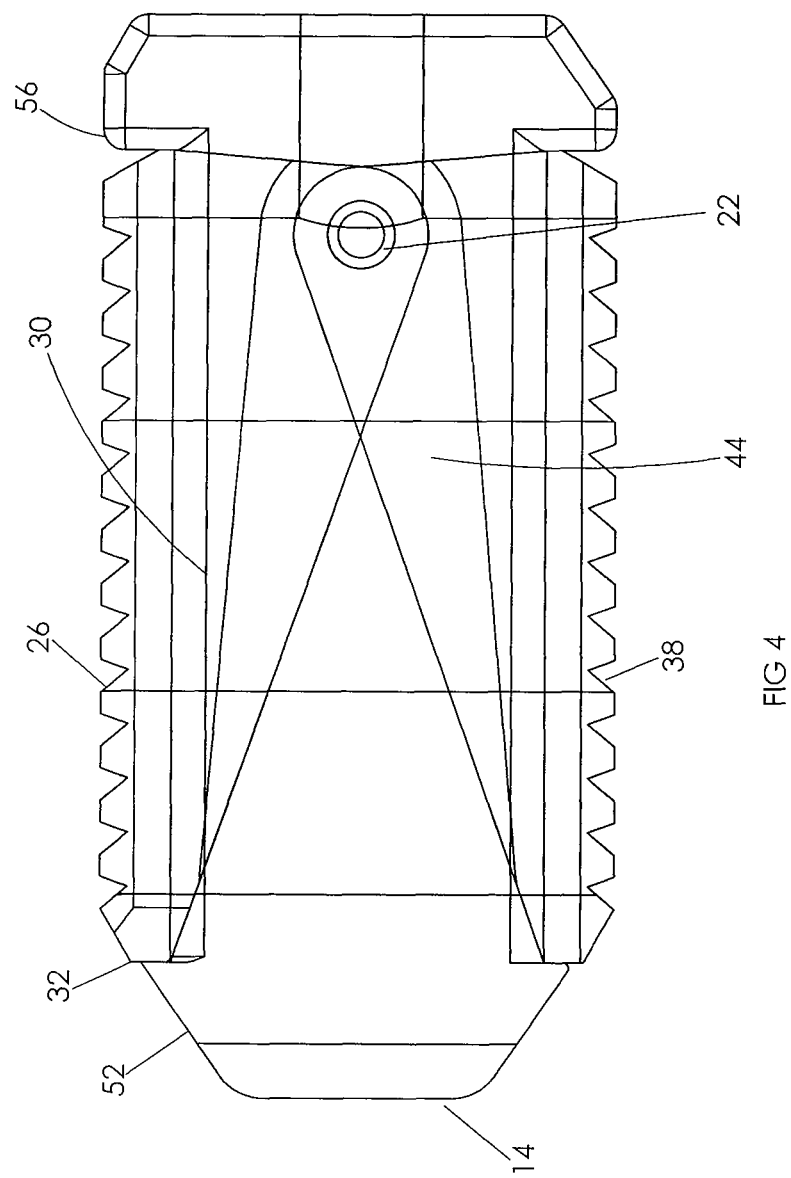

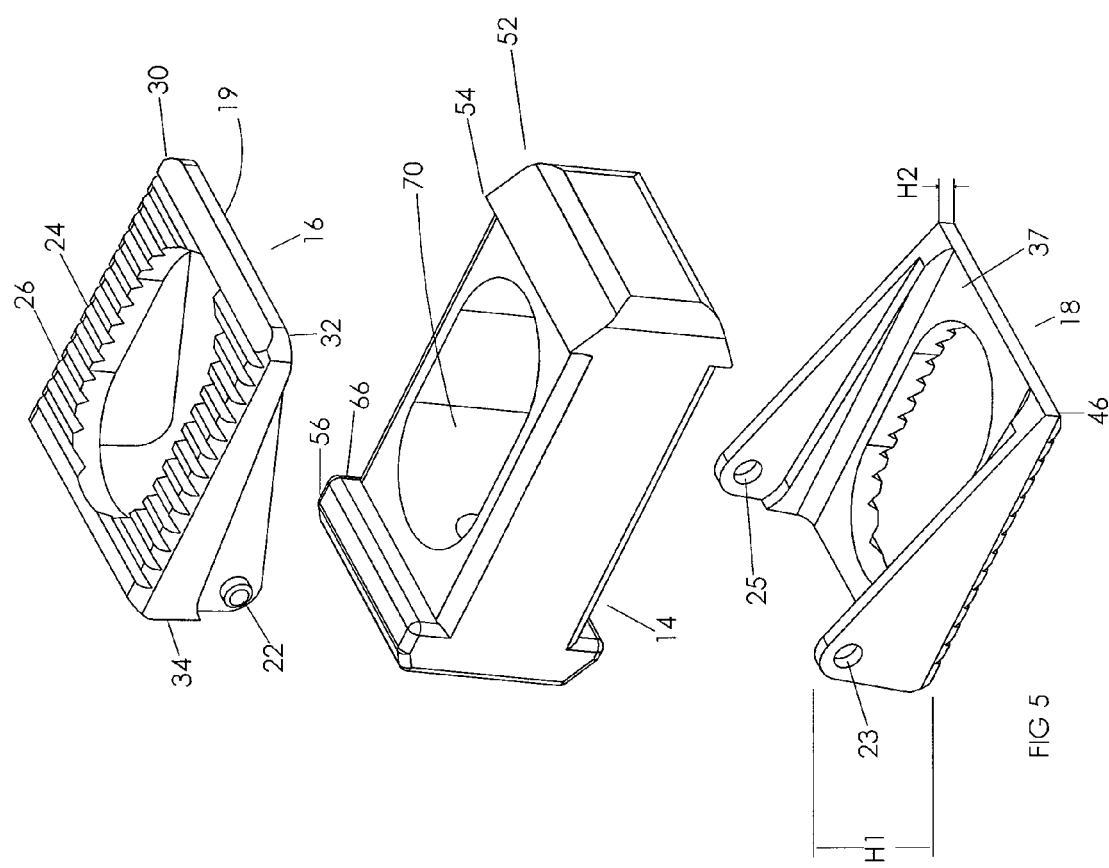

PLIF HINGED SPACER

PRIORITY CLAIM

In accordance with 37 C.F.R. 1.76, a claim of priority is included in an Application Data Sheet filed concurrently herewith. Accordingly, the present invention claims priority to U.S. Provisional Patent Application No. 61/800,739, filed on Mar. 15, 2013, entitled "PLIF Hinged Spacer", the contents of which are hereby expressly incorporated herein by reference.

FIELD OF THE INVENTION

This invention relates to the field of orthopedic surgery and, more particularly, to implants to be placed between vertebrae in the spine.

BACKGROUND OF THE INVENTION

Spinal stabilization is one approach to alleviating chronic back pain caused by displaced disk material or excessive movement of individual vertebrae. Conventional stabilization techniques include fusing two or more vertebrae together to circumvent or immobilize the area of excessive movement. Normally, the vertebral disk material which separates the vertebrae is removed and bone graft material is inserted in the space for interbody fusion. In addition to or, in place of, the bone graft material, a spinal implant may be inserted in the intervertebral space.

The conventional surgical approach for stabilization has been posteriorly for ease of access to the spine and to avoid interfering with internal organs and tissue. Usually the implant site is prepared to maintain natural lordosis and to accept a certain sized implant within certain pressure limits. This requires considerable time and skill by the surgeon.

U.S. Pat. No. 6,562,074 discloses a spinal insert which can be manipulated to adjust the height of the implant through links connected to the upper and lower plates.

U.S. Pat. No. 6,120,506 discloses a lordotic implant and a tap for use in preparing the vertebrae. The implant is designed to be inserted between the non-parallel end plates of adjacent vertebrae and maintain the natural lordotic angle of the spine. This is done through the use of a threaded tapered plug inserted in a tapped hole in the direction required by the lordosis of the spine. The implant is hollow and has radial apertures for accommodating bone graft material.

U.S. Pat. No. 6,015,436 discloses a tubular spinal implant. The implant is hollow and has radial apertures for interbody fusion through bone growth material. The device is placed between adjacent vertebrae with the opposite ends of the tube contacting the opposing vertebrae. The opposite ends are threaded together to form the hollow tube.

U.S. Pat. Nos. 7,211,112; 7,850,733 and 8,273,129 disclose opposing wedge ramp having a main body having upper and lower sections with mating sidewalls relatively movable along an inclined ramp. The inclined ramp forms a wedge movable between inclined sidewalls of the main body sections. The main body sections and the inclined ramp form a hollow cube-shaped structure with common open sides.

SUMMARY OF THE INVENTION

Disclosed is an implant formed from a hinged distractor and an insert body. The hinged distractor has an upper and lower support body that is hinged by use of pinions. The insert body is constructed and arranged to slide between the upper and lower support body to expand and maintain a space between the upper and lower support bodys. The spacer includes a leading edge that is tapered to allow ease of insertion. A trailing edge that extends beyond a front edge of the upper support body will cause the insert body to be locked into position. A trailing edge engages the rear of the upper support body to prevent over insertion. A lower surface of the spacer may include locking surfaces.

Accordingly, it is an objective of the instant invention to teach a posterior surgical approach for placement of a spinal implant for interbody fusion allowing the implant to be inserted through a small incision and increased in size in situ.

It is yet another objective of the instant invention to teach an implant facilitating interbody fusion through bone graft or an ingrowth-type implant.

Other objectives and advantages of this invention will become apparent from the following description taken in conjunction with any accompanying drawings; wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 2 is an exploded rear view of FIG. 1;
FIG. 3 is a perspective view of the spinal implant with the insert feeding into the distractor;
FIG. 4 is a cross sectional side view of the spinal implant;
FIG. 5 is an exploded view of the spinal implant.

DETAILED DESCRIPTION OF THE INVENTION

Figure 1:
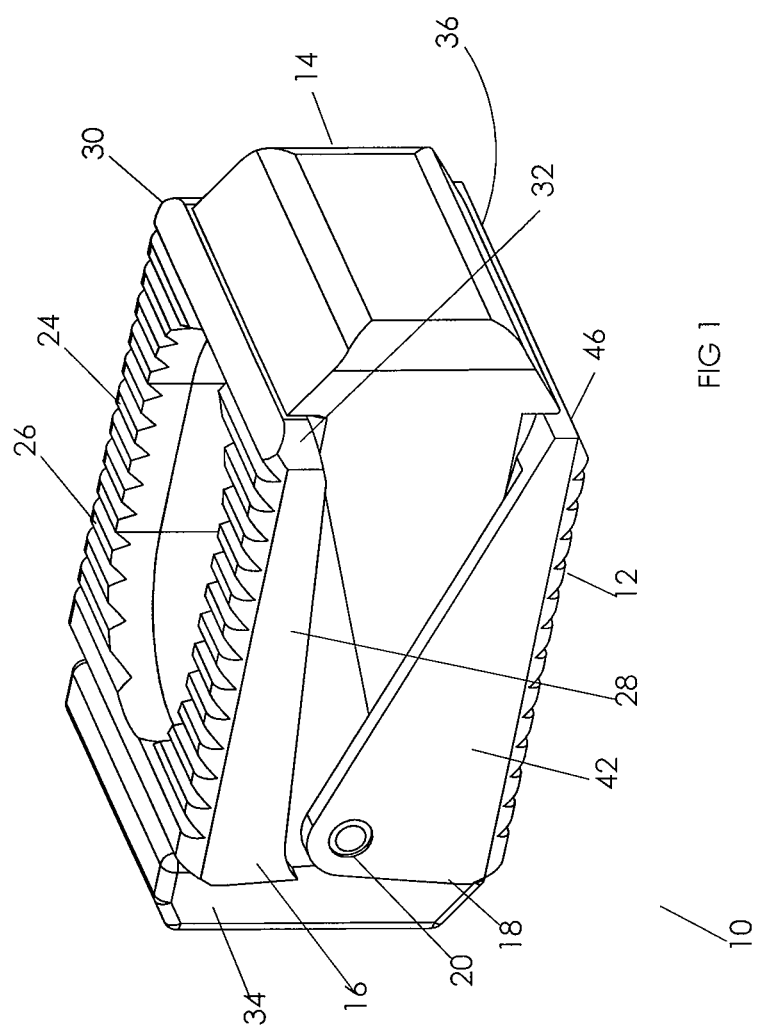
FIG. 1 is a perspective view of the spinal implant.

The spinal implant 10 is inserted in the intervertebral space to replace damaged, missing or excised disk material. This extended position allows the leading end of the distractor to be inserted in a small intervertebral space without the necessity of excising structurally sound bone.

Referring to the drawings, disclosed is an implant 10 formed from a hinged distractor 12 and an insert body 14. The hinged distractor 12 is defined by an upper support body 16 and a lower support body 18 that are hinged together by use of pinions 20 and 22 insertable into apertures 23 and 25. The upper support body 16 is formed from a substantially flat plate having an upper surface 24 to provide a large contact area with the vertebra and a lower surface 19 for use in abutting the insert body 14. The top surface 24 includes contact lands and grooves 26 to provide a better purchase although other stippled treatment may be employed. The upper support body 16 includes side walls 28 and 30 that are sloped from the front edge 32 to the rear edge 34. The slope of the walls illustrated by a first height h1 adjacent the proximal end of the plate and a second height h2 adjacent the distal end of the plate, the first height h1 greater than the second height h2.

Similarly, a lower support body 18 has an outer surface 36 to provide a large contact area with the vertebra and an inner surface 37 for use in abutting the insert body 14. The outer surface 36 includes contact lands and grooves 38 to provide a better purchase although other stippled treatment may be employed. The lower support body 18 is further defined by side walls 42 and 44 that are sloped from the front edge 46 to the rear edge 48. The outer surface 36 is a substantially flat plate to provide a large contact area with the vertebra. The lower and upper support body 12 and 16 are pivotable in relation to increase the distance between the front edges 30 and 46.

The distractor 12 upper support body 16 and lower support body 18 may be made of conventional materials used for surgical implants, such as stainless steel and its many different alloys, titanium, and any other metal with the requisite strength and biologically inert properties. Polymeric materials with adequate strength and biological properties may also be used in the construction of the distractor.

The insert body 14 is constructed and arranged to slide between the upper support body 16 and lower support body 18 to expand and maintain a space between the front edges 30 and 36. The insert body 14 having a leading edge 52 that is tapered to allow ease of insertion with light tamping. The leading edge 52 has a trailing edge 54 that extends beyond the front edge 32 of the upper support body 16 causing the insert body 14 to be locked into position. A trailing edge 56 engages the rear edge 34 of the upper support section 16. Similarly, a lower surface of the insert body 14 may include a leading edge 62 that is tapered to allow ease of insertion. The leading edge 62 has a trailing edge 64 that extends beyond the front edge 46 of the lower support body 18 causing the insert body to be locked into position along the top and bottom. Similarly a rear trailing edge 66 engages the rear edge 48 of the lower support body 18. The insert body 14 is preferably constructed from polyether ether ketone (PEEK), which is an organic polymer thermoplastic. The distractor and insert body are open to allow placement of bone growth material therein or otherwise provide quicker fusion to the bone. Shown are aperture 70 in the insert body 14 and aperture 72 in the distractor 12.

Figure 7:
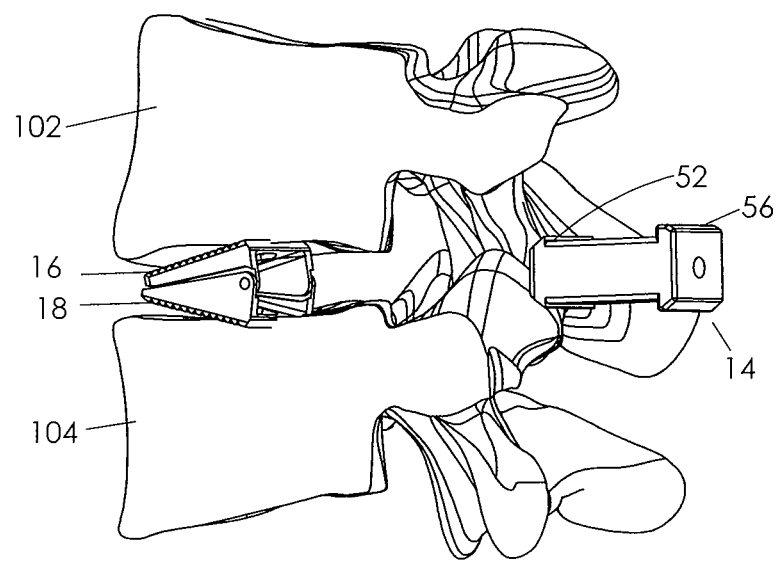
FIG. 7 is a pictorial view the spinal implant installed.
Figure 6:
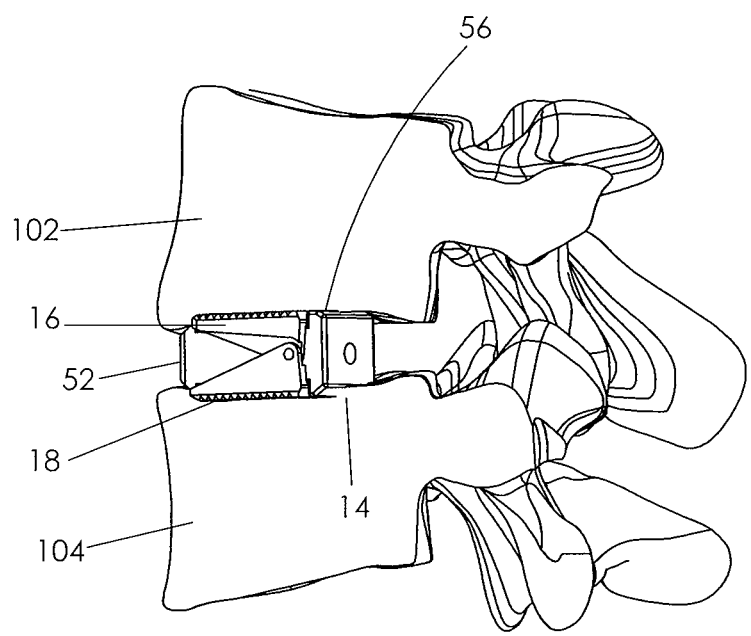
FIG. 6 is a pictorial view the insert body to be inserted into the distractor.

FIGS. 6 and 7 is a pictorial of the spinal implant in position for placement between vertebrae 102 and 104 with hinged distractor formed from the upper support body 16 and lower support body 18 placed into position. Insert body 14 having leading edge 52 is slidably inserted between said top and bottom plates of the upper and lower support body until the leading edge 52 and rear trailing edge is locked into position. The upper surface of the top plate and the outer surface of the bottom plate includes contact lands and grooves to frictionally engage the vertebral body. The distractor 12 is inserted between adjacent vertebrae and the insert body 14 placed into position providing a desired distance between the sections. The adjacent vertebrae are forced apart to equal the height of the implant. The spinal fusion device may be used unilaterally or bilaterally.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A spinal implant comprising:
   a hinged distractor formed from an upper support body having a substantially flat top plate defined by a proximal end and a distal end with spaced apart side edges, said top plate having an upper surface and a lower surface with first and second sloped walls extending from the lower surface having a first height adjacent the proximal end tapering to a second height adjacent the distal end pivotedly coupled to a lower support body having a substantially flat bottom plate defined by a proximal end and a distal end with spaced apart side edges, said bottom plate having an outer surface and an inner surface with first and second sloped walls extending from the inner surface having a first height adjacent the proximal end tapering to a second height adjacent the distal end said proximal end of said first and second sloped walls of said top plate includes outwardly facing pinions insertable into apertures on said proximal end of said first and second sloped walls of said bottom plate; and
   an insert body having a top surface, a bottom surface, opposing lateral sides, opposing anterior and posterior end walls and a substantially hollow center, said insert body having a leading edge for insertion between said plates and a trailing edge that extends beyond the distal end of said plates to prevent retraction of said insert body from between said plates upon insertion; said main body sized for slidable insertion between said top and bottom plate of said hinged distractor.

2. The spinal implant according to claim 1 wherein said first height of said walls is greater than said second height of said walls.

3. The spinal implant according to claim 1 wherein said upper surface of said top plate and said outer surface of said bottom plate are stippled.

4. The spinal implant according to claim 1 wherein said upper surface of said top plate and said outer surface of said bottom plate includes contact lands and grooves.

5. The spinal implant according to claim 1 wherein said leading edge is tapered to facilitate insertion between said plates.

6. The spinal implant according to claim 1 wherein said insert body includes a trailing tab sized to prohibit insertion between said plates.

7. The spinal implant according to claim 1 wherein said insert body is constructed from polyether ether ketone.

8. The spinal implant according to claim 1 wherein said insert body includes a centrally disposed aperture for receipt of bone growth material.

9. The spinal implant according to claim 1 wherein each said plate includes an aperture to facilitate bone growth material placed within said insert body to engage adjacent bone.

10. The spinal implant according to claim 1 wherein said hinged distractor and said insert body may be used unilaterally or bilaterally.

* * * * *